US012758693B2

(12) United States Patent
Yuds et al.

(10) Patent No.: US 12,758,693 B2
(45) Date of Patent: Oct. 13, 2026

(54) SYSTEM AND METHODS FOR DIALYSIS EFFLUENT POWER HARVESTING

(71) Applicants: Fresenius Medical Care Holdings, Inc., Waltham, MA (US); Fresenius Medical Care Deutschland Gmbh, Bad Homburg (DE)

(72) Inventors: David Yuds, Hudson, NH (US); Christian Schlaeper, Wehrheim (DE); Martin Crnkovich, Walnut Creek, CA (US)

(73) Assignees: Fresenius Medical Care Holdings, Inc., Waltham, MA (US); Fresenius Medical Care Deutschland Gmbh, Bad Homburg (DE)

( * ) Notice: Subject to any disclaimer, the term of this patent is extended or adjusted under 35 U.S.C. 154(b) by 240 days.

(21) Appl. No.: 18/768,740

(22) Filed: Jul. 10, 2024

(65) Prior Publication Data

US 2026/0014304 A1 Jan. 15, 2026

(51) Int. Cl.
*A61M 1/16* (2006.01)
*A61L 2/10* (2026.01)
(Continued)

(52) U.S. Cl.
CPC ............ *A61M 1/1601* (2014.02); *A61L 2/10* (2013.01); *A61M 1/155* (2022.05);
(Continued)

(58) Field of Classification Search
CPC .. A61M 1/1601; A61M 1/155; A61M 1/1627; A61M 1/363; A61M 1/367;
(Continued)

(56) References Cited

U.S. PATENT DOCUMENTS 11,701,456 B2 * 7/2023 Caluya .................... A61M 1/28 604/29
2013/0277307 A1 10/2013 Jensen
(Continued)

FOREIGN PATENT DOCUMENTS

EP 4158190 B1 * 8/2025 ............. C25B 15/08

OTHER PUBLICATIONS

Sejal Sharma, "New membrane generates electricity while filtering wastewater," Interesting Engineering, Mar. 2, 2023, 9 pages. [online source] URL: https://interestingengineering.com/innovation/membrane-clean-water-generate-electricity/ (Year: 2023).*
(Continued)

*Primary Examiner* — Rebecca E Eisenberg
*Assistant Examiner* — Gabriella E Burnette
(74) *Attorney, Agent, or Firm* — KDW Firm PLLC

(57) ABSTRACT

Provided herein are embodiments for a wearable or portable dialysis system. The wearable or portable dialysis system includes a dialysis machine including a pump to move dialysate through a filtering component thereof. The wearable or portable dialysis system further includes an electric circuit in communication with the dialysis machine for controlling electronic components of the dialysis machine. The filtering component includes an electricity generation and purification membrane (EPM) in a filtering path of the filtering component, and the EPM is coupled to the electric circuit. In response to dialysate moving through the filtering path of the filtering component, electricity is generated by the EPM and provided to the electric circuit to power the electronic components of the dialysis machine.

20 Claims, 9 Drawing Sheets

(51) Int. Cl.
*A61L 103/05* (2026.01)
*A61M 1/14* (2006.01)
*A61M 1/36* (2006.01)

(52) U.S. Cl.
CPC .......... *A61M 1/1627* (2014.02); *A61M 1/363* (2014.02); *A61M 1/367* (2013.01); *A61L 2103/05* (2026.01); *A61M 2202/0021* (2013.01); *A61M 2205/0233* (2013.01); *A61M 2205/10* (2013.01); *A61M 2205/125* (2013.01); *A61M 2205/50* (2013.01); *A61M 2205/7545* (2013.01); *A61M 2205/82* (2013.01); *A61M 2209/088* (2013.01)

(58) Field of Classification Search
CPC .. A61M 2202/0021; A61M 2205/0233; A61M 2205/10; A61M 2205/125; A61M 2205/50; A61M 2205/7545; A61M 2205/82; A61M 2209/088; A61M 2205/8212; A61M 2205/8237; A61M 1/1696; A61M 1/3679; A61M 1/1621; A61M 1/14; A61M 1/16; A61L 2/10; A61L 2103/05; C02F 1/4693; B01D 35/06; B01D 61/24–2461; B01D 61/42–423
See application file for complete search history.

(56) References Cited

U.S. PATENT DOCUMENTS

| | | | | |
|---|---|---|---|---|
| 2016/0199559 | A1 | 7/2016 | Glaser | |
| 2021/0252204 | A1 * | 8/2021 | Hogard ............... | A61M 1/1656 |
| 2025/0082830 | A1 * | 3/2025 | Gura ................... | A61M 1/3413 |

OTHER PUBLICATIONS

Yang Zou et al., "Recent progress in human body energy harvesting for smart bioelectronic system," Fundamental Research 1, May 5, 2021, 364-382.
Sejal Sharma, "New membrane generates electricity while filtering wastewater," Interesting Engineering, Mar. 2, 2023, 9 pages. [online source] URL: https://interestingengineering.com/innovation/membrane-clean-water-generate-electricity.
Ji-Soo Jang et al., "Bidirectional Water-Stream Behavior on a Multifunctional Membrane for Simultaneous Energy Generation and Water Purification," Advanced Materials, vol. 35, Issue7, Dec. 9, 2022, 6 pages.
International Search Report and Written Opinion for International Application No. PCT/US2025/028119, filing date May 7, 2025, 21 pages.

* cited by examiner

SYSTEM AND METHODS FOR DIALYSIS EFFLUENT POWER HARVESTING

FIELD OF DISCLOSURE

This disclosure generally relates to power harvesting, and more particularly, to a system and method for dialysis effluent power harvesting using an electricity generation and purification membrane to facilitate, for example, power and weight savings in wearable dialysis machines and/or systems.

BACKGROUND

Dialysis machines are used in the treatment of renal disease. The two principal dialysis methods are hemodialysis (HD) and peritoneal dialysis (PD). During HD, the patient's blood is passed through a dialyzer of an HD machine and/or system while also passing dialysate through the dialyzer. A semi-permeable membrane in the dialyzer separates the blood from the dialysate within the dialyzer and allows diffusion and osmosis exchanges to take place between the dialysate and the blood stream. During PD, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream.

Dialysis, both PD and HD, is a life sustaining therapy necessary when a person's kidneys can no longer naturally filter waste from the patient's bloodstream. HD is generally performed at a minimum of three times a week for those suffering end-stage renal disease (ESRD) and PD is generally performed daily, either overnight with a continuous cyclic peritoneal dialysis (CCPD) machine and/or system or during the day with a continuous ambulatory peritoneal dialysis (CAPD) machine and/or system. Generally speaking, dialysis is performed with the patient in a stationary position using complex and/or heavy, bulky equipment. In order to better integrate dialysis into a patient's lifestyle, wearable artificial kidneys are being developed to allow the patient to undergo dialysis while remaining mobile, untethered to power and/or dialysis-related fluids. Wearable artificial kidneys typically include a belt, a filter, a pump, a waste collector, and a power supply to perform the bare minimum of ambulatory dialysis throughout the day.

However, many of the currently available wearable artificial kidneys are heavy and/or cumbersome due to the weight of their batteries or power supplies. While there are some energy harvesting options available to supplement the power provided to the components of the wearable artificial kidneys, the panoply of energy harvesting technology is either poorly integrated into comfortable technology, uses special costly clothing, requires the wearer to be active, or can only produce power under certain conditions. Furthermore, current energy harvesting options often utilize batteries to store this intermittent electricity to provide power for the pump and sensors.

As such, there is a need for improved systems and methods for addressing some of the above-mentioned deficiencies.

BRIEF SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In some embodiments, a dialysis system is provided, the dialysis machine including a pump configured to move dialysate through a filtering component of the dialysis machine. The dialysis system further includes an electric circuit in communication with the dialysis machine and configured to control electronic components, including the pump, of the dialysis machine. The filtering component includes an electricity generation and purification membrane (EPM) in a filtering path of the filtering component, wherein the EPM is coupled to the electric circuit. In some embodiments, the EPM is configured to generate electricity in response to dialysate moving through the filtering path of the filtering component and provide the generated electricity to the electric circuit to power the electronic components of the dialysis machine.

In some embodiments, a wearable or portable dialysis system is provided, the wearable or portable dialysis machine including a dialysis machine including a pump configured to move dialysate through a filtering component of the dialysis machine. The wearable or portable dialysis machine further includes an electric circuit in communication with the dialysis machine and configured to control electronic components, including the pump, of the dialysis machine. The filtering component includes an electricity generation and purification membrane (EPM) in a filtering path of the filtering component, wherein the EPM is coupled to the electric circuit. In some embodiments, the EPM is configured to generate electricity in response to dialysate moving through the filtering path of the filtering component and provide the generated electricity to the electric circuit to power the electronic components of the dialysis machine.

In some embodiments, a method of powering electronic components in a dialysis machine is provided, the dialysis machine including a pump to move dialysate through a filtering component of the dialysis machine. In some embodiments, the method includes providing an electric circuit in communication with the dialysis machine for controlling electronic components thereof, including the pump. The method further includes arranging an electricity generation and purification membrane (EPM) in a filtering path of the filtering component, wherein the EPM is coupled to the electric circuit. In response to dialysate moving through the filtering path of the filtering component, the method further includes forwarding electric current produced by the EPM to the electric circuit to power the electronic components of the dialysis machine.

Non-transitory computer program products (i.e., physically embodied computer program products) are also described that store instructions, which, when executed by one or more data processors (i.e., processor circuit) of one or more computing systems, cause at least one data processor to perform operations herein. Similarly, computer systems are also described, which may include one or more data processors and memory coupled to the one or more data processors. The memory may temporarily or permanently store instructions that cause at least one processor to perform one or more of the operations described herein. In addition, methods can be implemented by one or more data processors, which are either within a single computing system or distributed among two or more computing systems. Such computing systems can be connected and can exchange data and/or commands or other instructions or the like via one or more connections, including but not limited to a connection over a network (e.g., the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE SEVERAL VIEWS OF THE DRAWINGS

By way of example, specific embodiments of the disclosed methods and devices will now be described, with reference to the accompanying drawings, in which.

Figure 1:
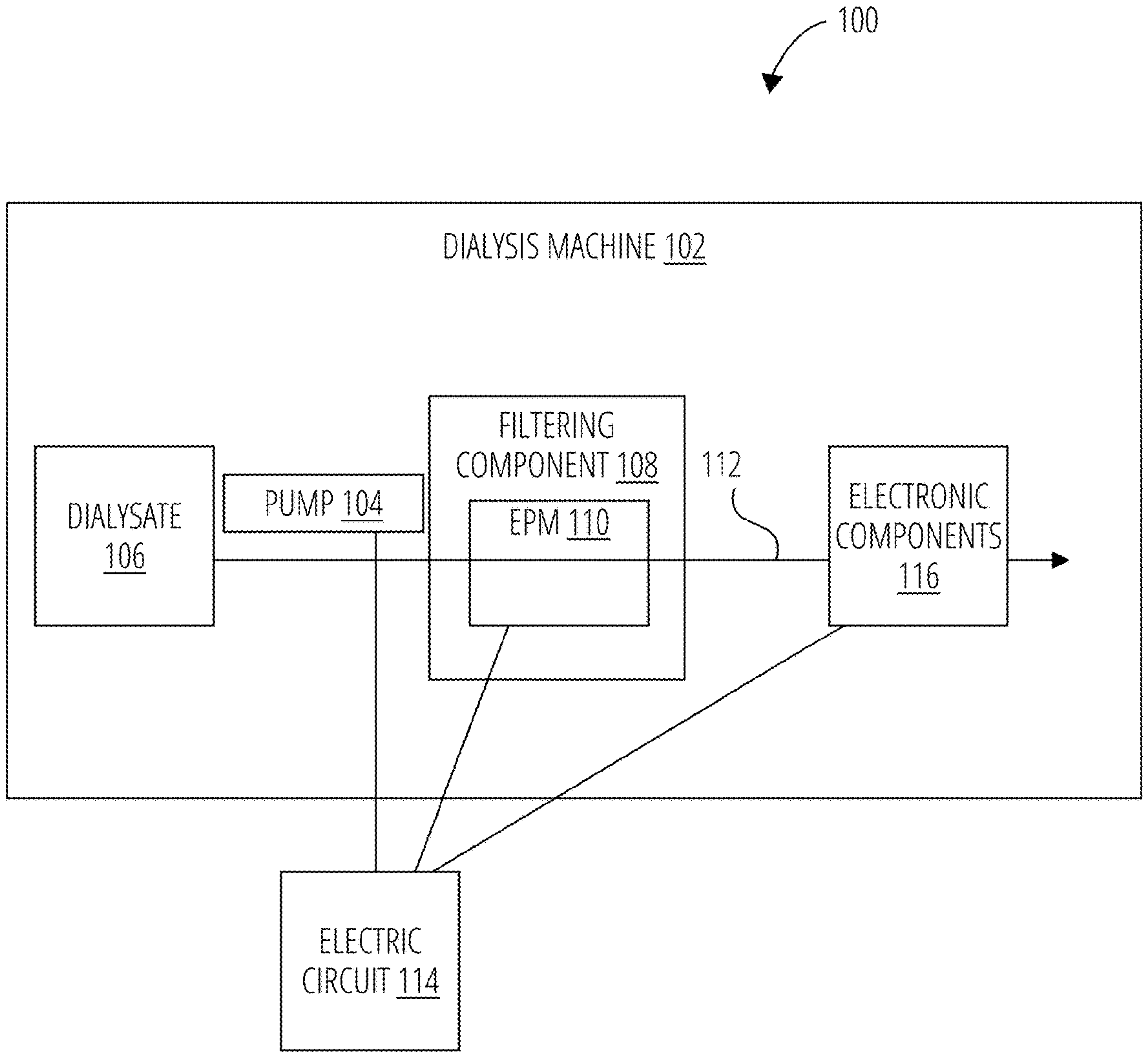
FIG. 1 is a block diagram of an exemplary embodiment of a dialysis system in accordance with one or more features of the present disclosure.

It should be understood that the drawings are not necessarily to scale and that the disclosed embodiments are sometimes illustrated diagrammatically and in partial views. In certain instances, details which are not necessary for an understanding of the disclosed methods and devices or which render other details difficult to perceive may have been omitted. It should be further understood that this disclosure is not limited to the particular embodiments illustrated herein. In the drawings, like numbers refer to like elements throughout unless otherwise noted.

DETAILED DESCRIPTION

With general reference to notations and nomenclature used herein, one or more portions of the detailed description which follows may be presented in terms of program procedures executed on a computer or network of computers. These procedural descriptions and representations are used by those skilled in the art to most effectively convey the substances of their work to others skilled in the art. A procedure is here, and generally, conceived to be a self-consistent sequence of operations leading to a desired result. These operations are those requiring physical manipulations of physical quantities. Usually, though not necessarily, these quantities take the form of electrical, magnetic, or optical signals capable of being stored, transferred, combined, compared, and otherwise manipulated. It proves convenient at times, principally for reasons of common usage, to refer to these signals as bits, values, elements, symbols, characters, terms, numbers, or the like. It should be noted, however, that all of these and similar terms are to be associated with the appropriate physical quantities and are merely convenient labels applied to those quantities.

Useful machines for performing operations of various embodiments include digital computers as selectively activated or configured by a computer program stored within that is written in accordance with the teachings herein, and/or include apparatus specially constructed for the required purpose or a digital computer. Various embodiments also relate to apparatus or systems for performing these operations. These apparatuses may be specially constructed for the required purpose. The required structure for a variety of these machines will be apparent from the description given.

Embodiments of the present disclosure will now be described more fully hereinafter with reference to the accompanying drawings, in which several exemplary embodiments are shown. The subject matter of the present disclosure, however, may be embodied in many different forms and types of methods, systems, and devices for dialysis treatments and other potential medical devices and treatments, and should not be construed as limited to the embodiments set forth herein. Rather, these embodiments are provided so that this disclosure will be thorough and complete, and willfully convey the scope of the subject matter to those skilled in the art.

FIG. 1 is a block diagram of an exemplary embodiment of a dialysis system 100 in accordance with one or more features of the present disclosure. In use, the dialysis system 100 implements a dialysis effluent power harvesting system to generate at least some of the power for operating electronic components 116 of the dialysis system 100. In some embodiments, the dialysis system 100 includes a dialysis machine 102 including a pump 104 configured to move dialysate 106 through a filtering component 108 of the dialysis machine 102. In some embodiments, the dialysis system 100 includes an electric circuit 114 in communication with the dialysis machine 102 configured to control electronic components of the dialysis machine 102 including the pump 104. As discussed in further detail below, in some embodiments, the filtering component 108 includes an electricity generation and purification membrane (EPM) 110 in a filtering path 112 of the filtering component 108. In some embodiments, the EPM 110 is coupled to the electric circuit 114, and, in response to dialysate 106 moving through the filtering path 112 of the filtering component 108, the EPM 110 is configured to generate electricity and provide the generated electricity to the electric circuit 114 to power the electronic components of the dialysis machine.

In FIG. 1, the pump 104 and filtering component 108 are depicted separately from the electronic components 116. However, those having ordinary skill in the art will appreciate that the electronic components 116 can include the pump 104, the filtering component 108, and any other suitable electronic components 116. The electronic components 116 are called out separately to depict other possible components other than the pump 104 and the filtering component 108.

Additionally, FIG. 1 depicts the pump 104, the dialysate 106, the filtering component 108, the EPM 110, and the electronic components 116 as being collocated within the dialysis machine 102. However, in some embodiments, any of these devices may be separate from the dialysis machine 102, but just connected thereto using hoses, tubes, or wires, where appropriate.

In some embodiments, the dialysis machine 102 can be an HD machine or a PD machine. The dialysate 106 can be housed in any suitable reservoir, such as a container, canister, jar, jug, pouch, storage, tank, or vessel. The pump 104 can include any suitable pump that pumps dialysate 106 and/or blood through the dialysis machine 102 or any other suitable mechanism now known or hereafter developed for pumping dialysate 106 and/or blood for a dialysis machine 102. For example, in some embodiments, the pump 104 of the dialysis machine 102 includes a low power micropump for pumping dialysate 106 and blood through the dialysis machine 102. Those having ordinary skill in the art will understand that the patient's blood and the dialysate 106 will pump through the dialysis machine 102 in separate tubing, that is, tubing circuits that are separated from each other such that the dialysate 106 and the patient's blood does not mix.

In some embodiments, the filtering component 108 can include any suitable filtering component as discussed below, including a dialyzer, a sorbent cartridge, or any other suitable mechanism now known or hereafter developed for filtering dialysate or other liquid in a dialysis machine 102. In some embodiments, the pump 104 is configured to pump the dialysate 106 through the dialysis machine 102 including in the filtering path 112.

The filtering path 112 is a path of fluid flowing through the filtering component 108. The filtering path 112 includes the path fluid takes as it enters the filtering component 108, moves therethrough, and then egresses the filtering component 108.

In some embodiments, the electric circuit 114 is used to power one or more of the components of the dialysis machine 102. That is, the electric circuit 114 includes a power supply (e.g., battery, power supply with an AC-to-DC converter that connects to a wall outlet, or any other suitable mechanism now known or hereafter developed for powering electronics) and one or more electrical components to direct electrical current to electronic components 116 of the dialysis machine 102 to provide power thereto. In some embodiments, the electric circuit 114 includes a switch to allow or terminate the flow of current to the electronic components 116 on the dialysis machine 102. In some other embodiments, the electric circuit 114 includes a transistor or microelectromechanical system (MEMS). In some embodiments, the electric circuit 114 includes one or more operational amplifiers or a digital switch for switching current to power the pump 104, filtering component 108, or electronic components 116.

In some embodiments, the electric circuit 114 directs current to the pump 104 to power the pump 104 and cause the dialysate 106 and other fluids to flow through the dialysis machine 102. In other embodiments, the electric circuit 114 is configured to power the filtering component 108, including a sorbent cartridge. In some embodiments, the electric circuit 114 is configured to provide power to any other suitable electronic components 116 on the dialysis machine 102. For example, the electric circuit 114 may be configured to provide power to one or more auxiliary pumps, a shuttle pump, a display, one or more indicator light emitting diodes (LEDs), a bubble trap, a fan, or any other suitable electronic device on the dialysis machine 102 now known or hereafter developed.

In some embodiments, the electric circuit 114 is integrated with the dialysis machine 102 and located on an exterior of or within a housing of the dialysis machine 102. In some other embodiments, the electric circuit 114 is located separate from the dialysis machine 102 and connected thereto using a wire or a plurality of wires connected between the electric circuit 114 and the electronic components 116 including the pump 104 and the filtering component 108 and other electronics discussed herein.

In some embodiments, the electronic components 116 may include an ultraviolet (UV) LED powered by the electric circuit 114 or by electricity provided by the EPM 110 as discussed below. In some embodiments, the UV LED may be positioned in the filtering path 112 of the dialysate 106 and configured to destroy bacteria and viruses in the dialysate 106.

In some further embodiments, the electronic components 116 may include one or more components that are configured to produce an electric field around a portion of the filtering path 112 to remove toxins from the dialysate 106. For example, in some embodiments, the electronic components 116 include components that generate an electric charge or a time-varying electric current. In some embodiments, the electronic components 116 may include a capacitor or parallel plate electrodes that generate an electric field.

Figure 2A:
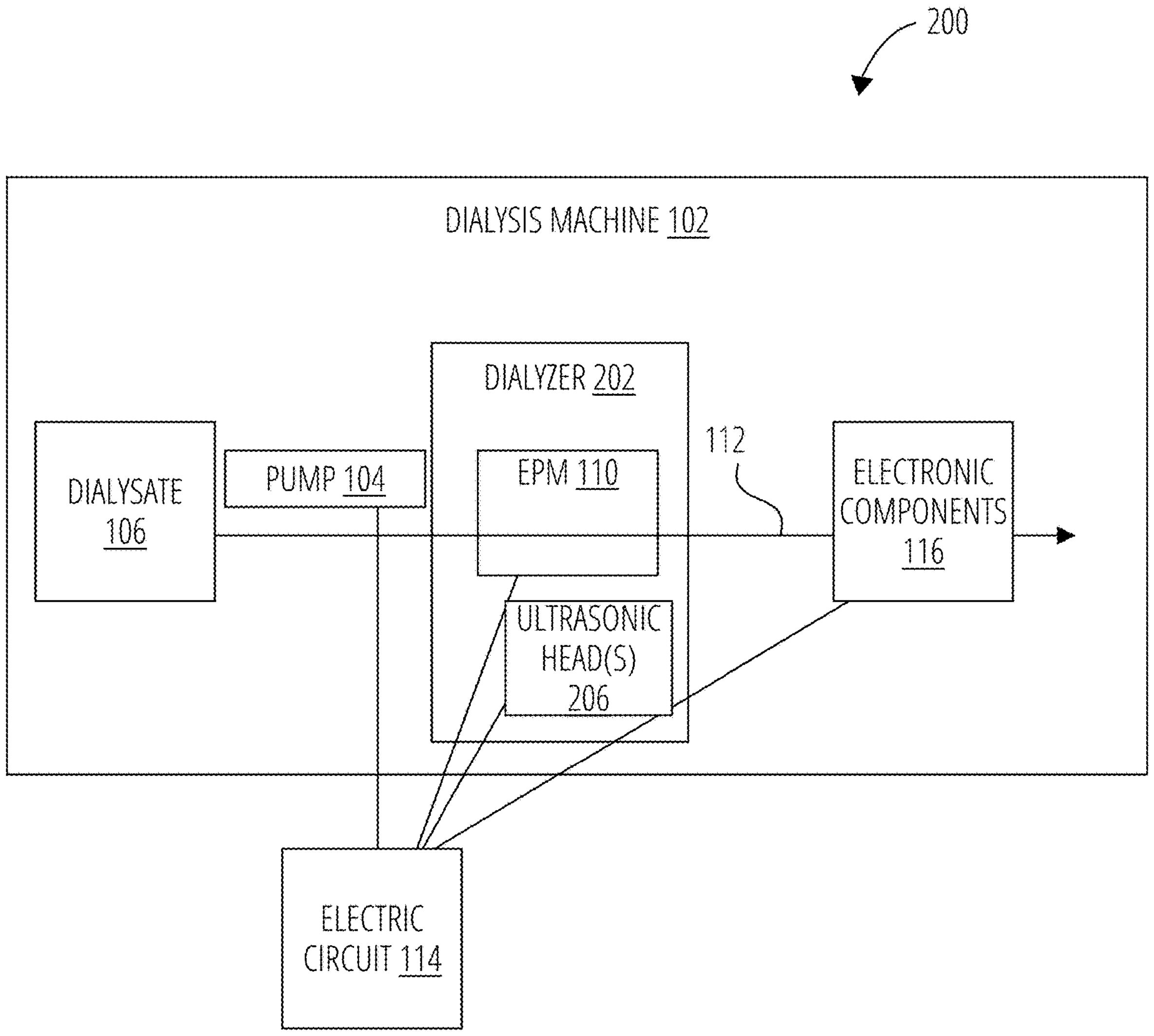
FIG. 2A is a block diagram of an alternate exemplary embodiment of a dialysis system in accordance with one or more features of the present disclosure.

FIG. 2A is a block diagram of an alternate exemplary embodiment of a dialysis system 200 in accordance with one or more features of the present disclosure. In use, dialysis system 200 is substantially similar to the dialysis system 100 from FIG. 1. However, as illustrated, dialysis system 200 includes a filtering component 108, which includes a dialyzer 202. In some embodiments, the electronic components 116 may include one or more ultrasonic head(s) 206 positioned within the dialyzer 202 and configured to eliminate air bubbles in the dialysate 106. For example, the ultrasonic head(s) 206 may produce ultrasonic waves that cause gas bubbles in the dialysate 106 to coalesce and form larger bubbles. These bubbles eventually get large enough to rise out of the liquid and release into the environment.

In some embodiments, the dialyzer 202 is in the flow path of the dialysate 106 as it flows through the dialysis machine 102, including through the dialyzer 202. Those having ordinary skill in the art will appreciate that both the blood from the patient and the dialysate 106 flow through the dialyzer 202. In use, the dialyzer 202 uses the dialysate 106 to remove toxins and waste from the patient's blood using diffusion.

Figure 3A:
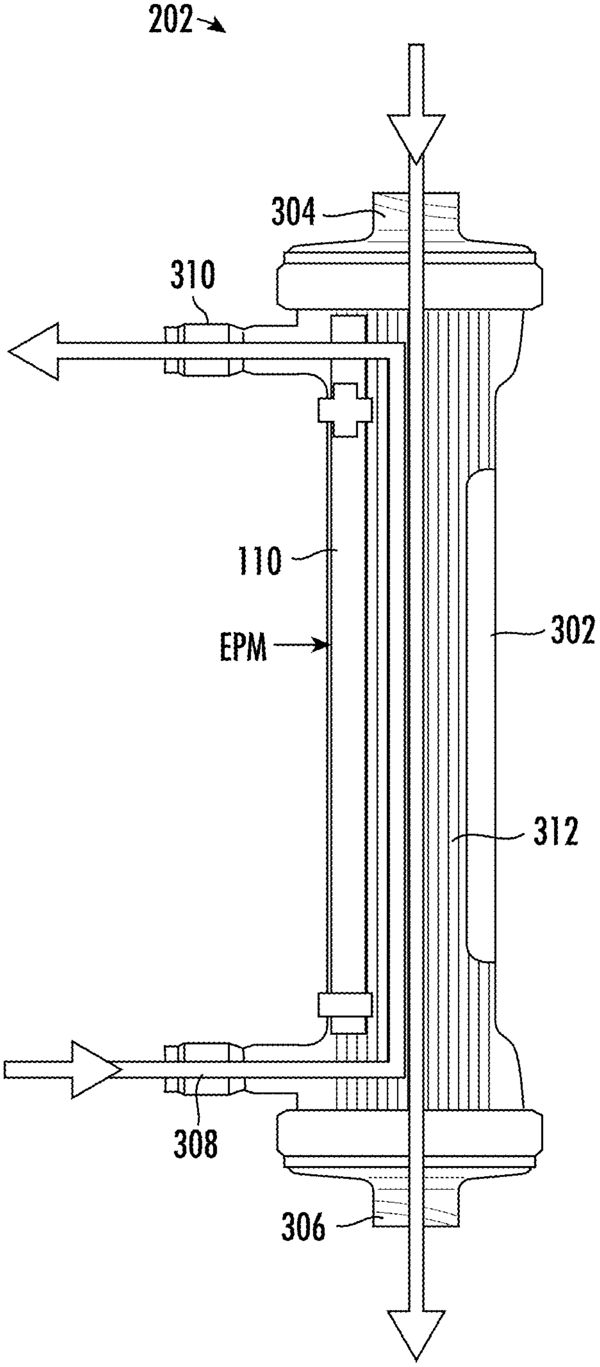
FIG. 3A illustrates an exemplary embodiment of a dialyzer in accordance with one or more features of the present disclosure.

In some embodiments, the EPM 110 may be positioned within the dialyzer 202 as described below. Thus arranged, as the dialysate 106 flows through the EPM 110 and the dialyzer 202, electricity is generated and provided to the electric circuit 114. FIG. 3A provides more details on an example embodiment of the dialyzer 202.

Figure 2B:
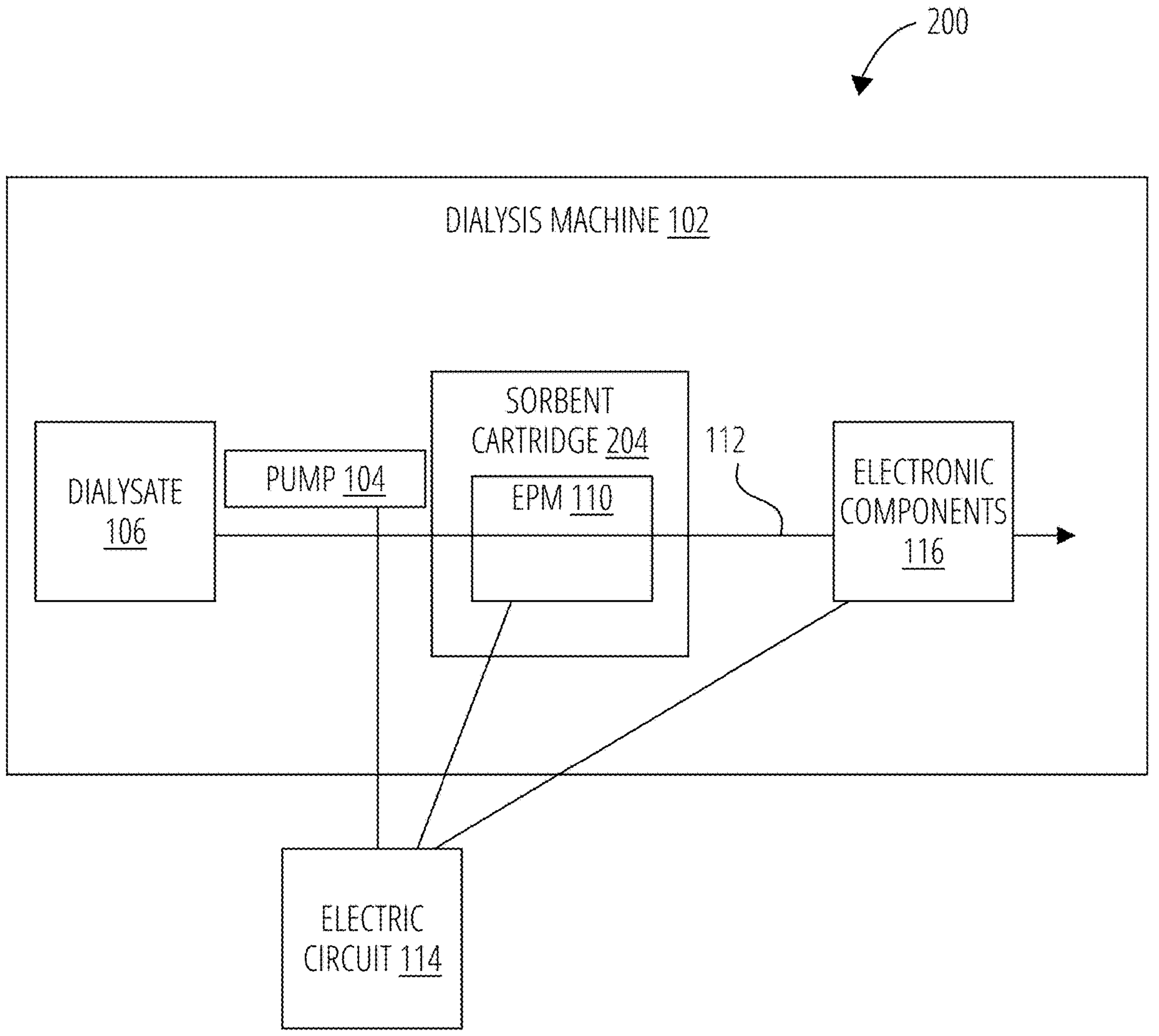
FIG. 2B is a block diagram of an alternate exemplary embodiment of a dialysis system in accordance with one or more features of the present disclosure.

FIG. 2B is a block diagram of an alternate exemplary embodiment of a dialysis system 200 in accordance with one or more features of the present disclosure. In use, dialysis system 200 is substantially similar to the dialysis system 100 from FIG. 1 and dialysis system 200 from FIG. 2A. However, as illustrated, dialysis system 200 includes a filtering component 108 including a sorbent cartridge 204. A sorbent cartridge may be used by the dialysis system 200 to treat or refresh the dialysate 106, thereby removing urea and other toxins and wastes from the dialysate 106 so that the dialysate 106 can be used for a longer period of time. That is, as the dialysate 106 is used to filter the patient's blood, the dialysate 106 will eventually become saturated with toxins, waste, and urea, and will not be as efficient at absorbing toxins from the patient's blood through diffusion. The sorbent cartridge 204 is a cartridge which the dialysate 106 flows through and the cartridge filters the dialysate of toxins, waste, and urea. The sorbent cartridge 204 can just be changed out over time instead of the dialysate 106. In some embodiments, the sorbent cartridge 204 may be in the flow path of the dialysate 106 as it flows through the dialysis machine 102, including through the sorbent cartridge 204. As such, the dialysate 106 is able to be reused.

Figure 3B:
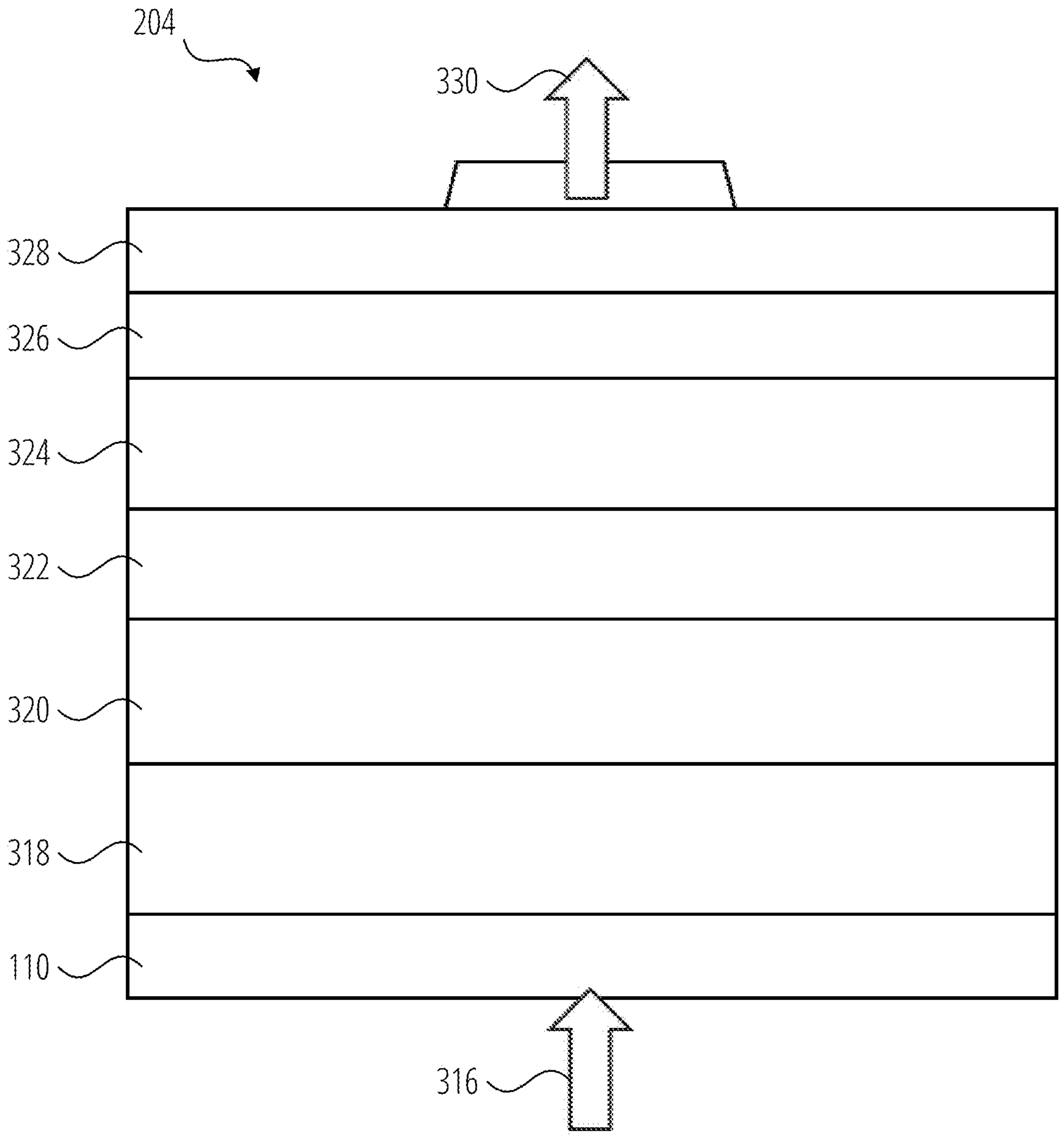
FIG. 3B illustrates an exemplary embodiment of a sorbent cartridge in accordance with one or more features of the present disclosure.

In some embodiments, the EPM 110 may be positioned within the sorbent cartridge 204, or integrated therewith, as described below. Thus arranged, as the dialysate 106 flows through the EPM 110 and the sorbent cartridge 204, electricity is generated and provided to the electric circuit 114. FIG. 3B provides more details on an example embodiment of a sorbent cartridge 204.

FIG. 3A illustrates an example dialyzer 202 as described above in FIG. 2A. In some embodiments, the dialyzer 202 includes an outer housing 302 that acts as a reservoir for the dialysate 106 as it flows through the dialyzer 202. In some embodiments, the dialyzer 202 further includes an ingress blood port 304, an egress blood port 306, an ingress dialysate port 308, and an egress dialysate port 310.

In some embodiments, the dialyzer 202 may further include an internal chamber (e.g., the cylindrical body of the dialyzer 202 may be hollow and has an internal chamber therein). In some embodiments, the internal chamber includes a plurality of tubes 312 extending between the ingress blood port 304 and the egress blood port 306. In some embodiments, the plurality of tubes 312 are arranged and configured to move the blood from the ingress blood port 304 to the egress blood port 306. In some embodiments, the plurality of tubes 312 may be made of semi-permeable membranes to enable toxins and waste to exit the semi-permeable membrane but allow blood to stay within the tubes 312.

In some embodiments, the internal chamber includes the dialysate flow path that includes the dialysate 106 flowing into the internal chamber through the ingress dialysate port 308, then around the plurality of tubes (e.g., within the internal chamber) to carry the waste out the semi-permeable membrane, away from the blood, and out the internal chamber through the egress dialysate port 310. That is, the dialysate flow path extends around the plurality of tubes such that, during operation of the dialysis system, the dialysate 106 carries the waste out the semi-permeable membrane, away from the blood, and out the internal chamber through the egress dialysate port. The dialysate 106 draws the toxins and waste from the blood using diffusion.

In some embodiments, the EPM 110 may be positioned within the internal chamber of the dialyzer 202 such that, during operation of the dialysis system, the dialysate 106 flows through the EPM 110 to get to the egress dialysate port 310. In some other embodiments, the EPM is positioned such that, during operation of the dialysis system, the dialysate 106 flows through the EPM 110 as it flows into the dialysate ingress port 308 and into the internal chamber. In some embodiments, the EPM 110 can be positioned such that dialysate 106 flows through the EPM 110 coming into the internal chamber (i.e., through the dialysate ingress port 308) and leaving the internal chamber (i.e., leaving the chamber out the dialysate egress port 310). The EPM 110 can be connected back to the electric circuit 114 of the dialysis machine 102 so that any power generated by the EPM 110 is provided back to the electric circuit 114 so that the electric circuit 114 can then provide the power to other electronic components 116 in the dialysis machine 102.

FIG. 3B illustrates an example embodiment of a sorbent cartridge 204 having various layers, which are described in more detail below. As described above, in some embodiments, the dialysis machine 102 includes a sorbent cartridge 204 to refresh dialysate. As the dialysate 106 absorbs the toxins and waste from the blood, the dialysate 106 gets contaminated with the waste and toxins. Running clean or fresh dialysate 106 through the dialyzer 202 will improve the ability of the dialysate 106 to remove toxins because the concentration of toxins in the dialysate 106 will be much less, allowing diffusion to work more efficiently.

In some embodiments, in addition to, or alternatively to the dialyzer 202, the filtering component 108 may include the sorbent cartridge 204. In such embodiments, the sorbent cartridge 204 includes various layers. For example, the sorbent cartridge 204 may include the EPM 110 positioned at an ingress port 316. The sorbent cartridge 204 may further include various layers for filtering the dialysate 106 as the dialysate flows therethrough. For example, the sorbent cartridge 204 may include a first activated carbon layer 318, a urease layer 320, a second activated carbon layer 322, a zirconium phosphate 324 layer, a zirconium oxide 326 layer, and a sodium bicarbonate 328 layer. Each of these layers act to filter one or more components of the wastes and toxins out of the dialysate 106 as the dialysate 106 flows through the sorbent cartridge 204.

In some embodiments, although FIG. 3B depicts the EPM 110 layer at the ingress port 316, the EPM 110 can also be positioned at an egress port 330 of the sorbent cartridge 204, or a combination thereof, such that dialysate 106 flows through the EPM 110 before exiting the sorbent cartridge 204. The EPM 110 can be connected back to the electric circuit 114 of the dialysis machine 102 so that any power generated by the EPM 110 is provided back to the electric circuit 114 so that the electric circuit 114 can then provide the power to other electronic components 116 in the dialysis machine 102.

In some embodiments, multiple EPMs 110 can be employed, whereby each of the EPMs 110 are connected back to the electric circuit 114 to provide power thereto. For example, one or more EPMs 110 can be provided in the dialyzer 202 and one or more EPMs 110 can be provided in the sorbent cartridge 204. Each of the EPMs 110 can be connected back to the electric circuit 114 to provide power thereto. Alternatively, the EPMs 110 can be connected directly to the electronic components 116 to supply power directly to the connected electronic component. For example, one or more EPMs 110 can be connected to a low power micropump configured to pump dialysate and blood through the dialysis machine to provide power thereto.

Figure 4:
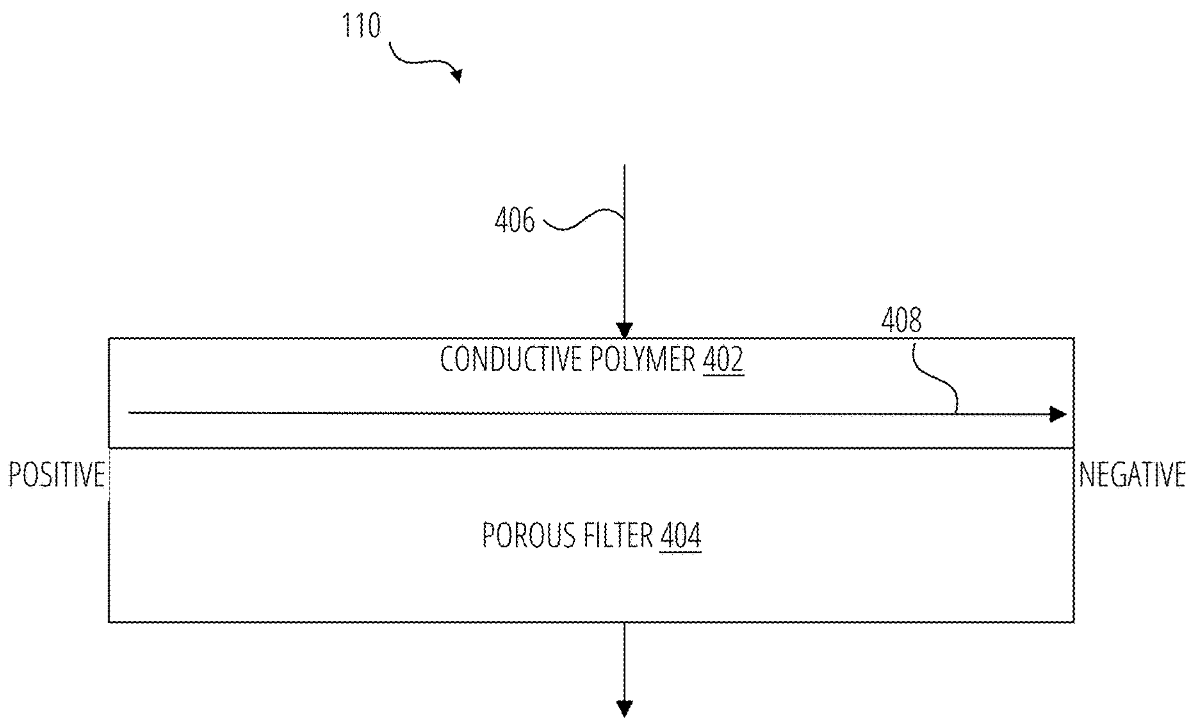
FIG. 4 illustrates an exemplary embodiment of an electricity generation and purification membrane in accordance with one or more features of the present disclosure.

FIG. 4 illustrates an exemplary embodiment of an EPM 110. For example, the EPM 110 may include at least a first layer including a conductive polymer 402 and a second layer, the second layer including a porous filter 404 configured to remove waste from the dialysate 106 and desilt dialysate passing therethrough. In some embodiments, the direction of dialysate flow 406 includes the dialysate 106 entering the conductive polymer 402 of the EPM 110 first and then exiting the porous filter 404.

In some embodiments, the conductive polymer 402 may include water-streaming carbon nanotubes configured such that, as dialysate 106 flows through the first layer (e.g., the conductive polymer 402), the water-streaming carbon nanotubes generate a movement of ions across the first layer of the EPM 110 in a direction that is perpendicular to a flow of dialysate (e.g., direction of ion flow 408) through the EPM 110. In some embodiments, the movement of ions generates the electricity that is provided to the electric circuit 114 or some of the other components of the dialysis machine 102, including the pump 104 or a low power micropump. As the ions flow across the conductive polymer 402, this generates a flow of current which can be directed to the electric circuit 114 via conductive wires or other materials connecting the EPM 110 to the electric circuit 114 or the electronic components 116.

In some embodiments, the EPM 110 may further include a poly(acrylic acid)/carboxymethyl cellulose (PAA/CMC) binder. In some embodiments, the EPM 110 can be made using graphene oxide. In some embodiments, the EPM 110 may include material that is printed in rigid sheets that can be applied to other surfaces, used by itself, or applied directly onto existing membranes or surfaces. In some embodiments, the EPM 110 is made of a flexible material. In some embodiments, the EPM 110 can have a thickness of between 0.01 mm to 0.15 mm. In some embodiments, the EPM 110 can have a thickness of between 0.05 mm to 0.1 mm. In some embodiments, multiple EPMs 110 can be layered on top of each other.

Figure 5A:
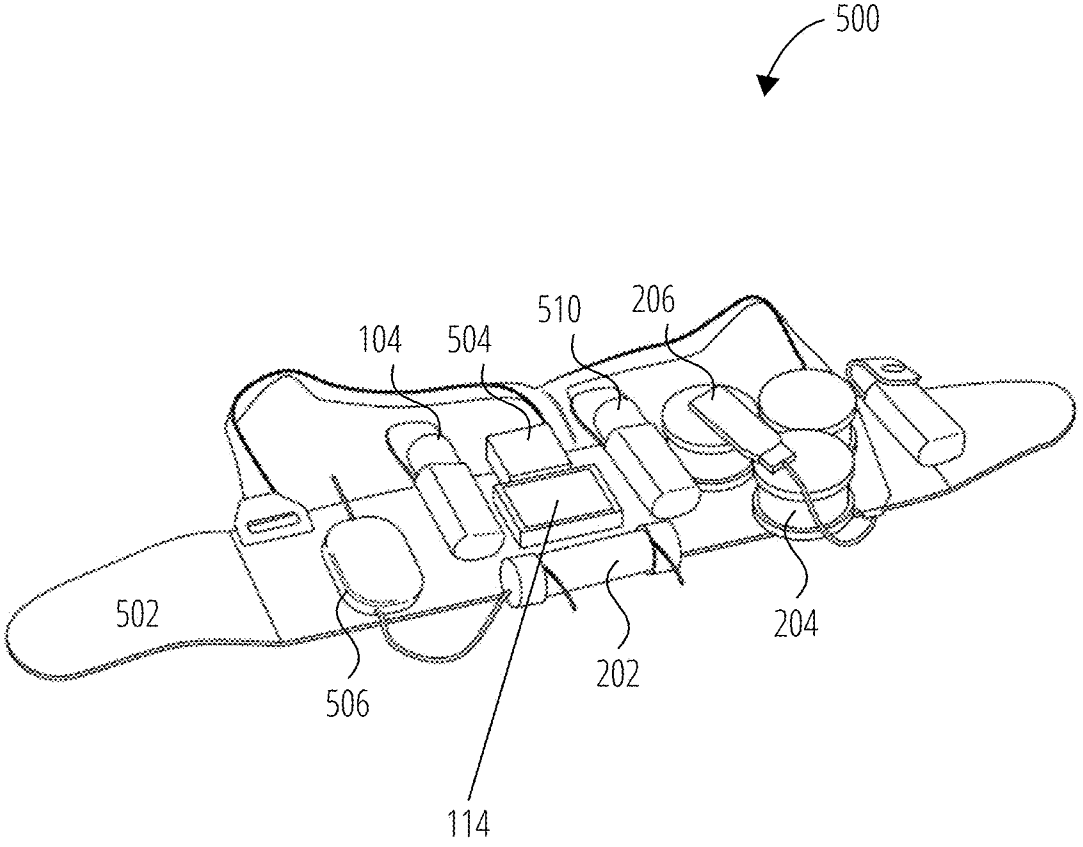
FIG. 5A illustrates an exemplary embodiment of a wearable dialysis system in accordance with one or more features of the present disclosure.

FIG. 5A illustrates an example embodiment of a wearable or portable dialysis system 500 in accordance with one or more features of the present disclosure. As illustrated, in some embodiments, the wearable or portable dialysis system 500 includes a dialysis machine 102 including one or more pumps 104 to move dialysate 106 through a filtering component 108 of the dialysis machine 102, similar to the components described above in FIG. 1. In some embodiments, the wearable or portable dialysis system 500 includes an electric circuit 114, similar to the electric circuit 114 in FIG. 1 above, the electric circuit 114 being in communication with the dialysis machine 102 for controlling electronic components 116 including the pump 104 of the dialysis machine 102.

In some embodiments, the filtering component 108 includes an electricity generation and purification membrane (EPM) 110 in a filtering path of the filtering component 108, wherein the EPM 110 is coupled to the electric circuit 114. In some embodiments, in response to dialysate 106 moving through the filtering path of the filtering component 108, electricity is generated by the EPM 110 and provided to the electric circuit 114 to power the electronic components 116 of the dialysis machine 102.

As shown in FIG. 5A, in some embodiments, the wearable or portable dialysis system 500 may include a wearable belt 502 having a kinetic-based power generator 504 thereon to initially power the pump 104 to start dialysate 106 flowing therethrough. In some embodiments, the kinetic-based power generator 504 provides power to the electric circuit 114 as a patient wearing the wearable belt 502 moves. In some embodiments, the wearable or portable dialysis system 500 may further include a battery 506 for providing power to the electric circuit 114. As depicted in FIG. 5A, the wearable or portable dialysis system 500 may also include a sorbent cartridge or array of cartridges 204 for filtering the dialysate as discussed above. The sorbent cartridge(s) 204 may include an EPM 110 (e.g., each cartridge may include an EPM 110, if multiple sorbent cartridges are present). In some embodiments, the wearable or portable dialysis system 500 may also include one or more auxiliary pump(s) 510 in case the primary pump 104 malfunctions.

Figure 5B:
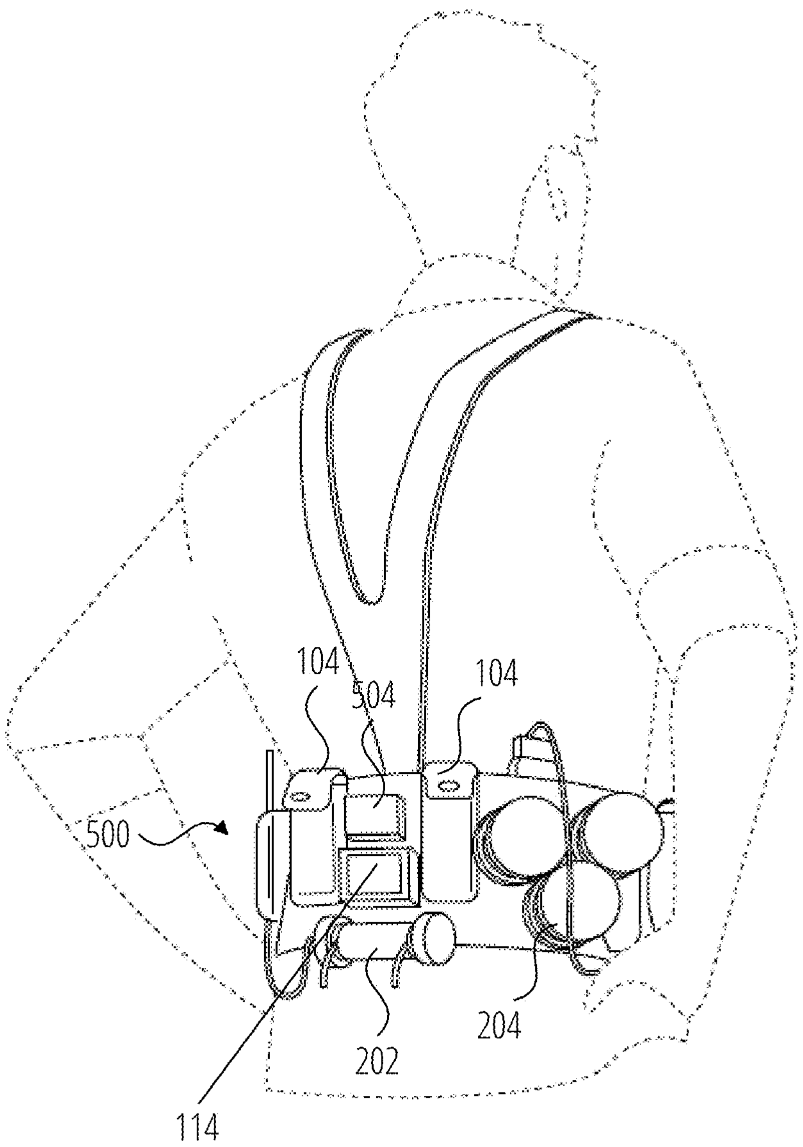
FIG. 5B illustrates an exemplary embodiment of a wearable dialysis system in accordance with one or more features of the present disclosure.

FIG. 5B illustrates a person wearing the wearable or portable dialysis system 500 of FIG. 5A. Although the wearable or portable dialysis system 500 is depicted here as including a wearable belt 502, in some embodiments, the wearable or portable dialysis system 500 is integrated into one or more of the following a wearable belt, a backpack, a waist pack, and a vest wearable around a person's back and torso.

Figure 6:
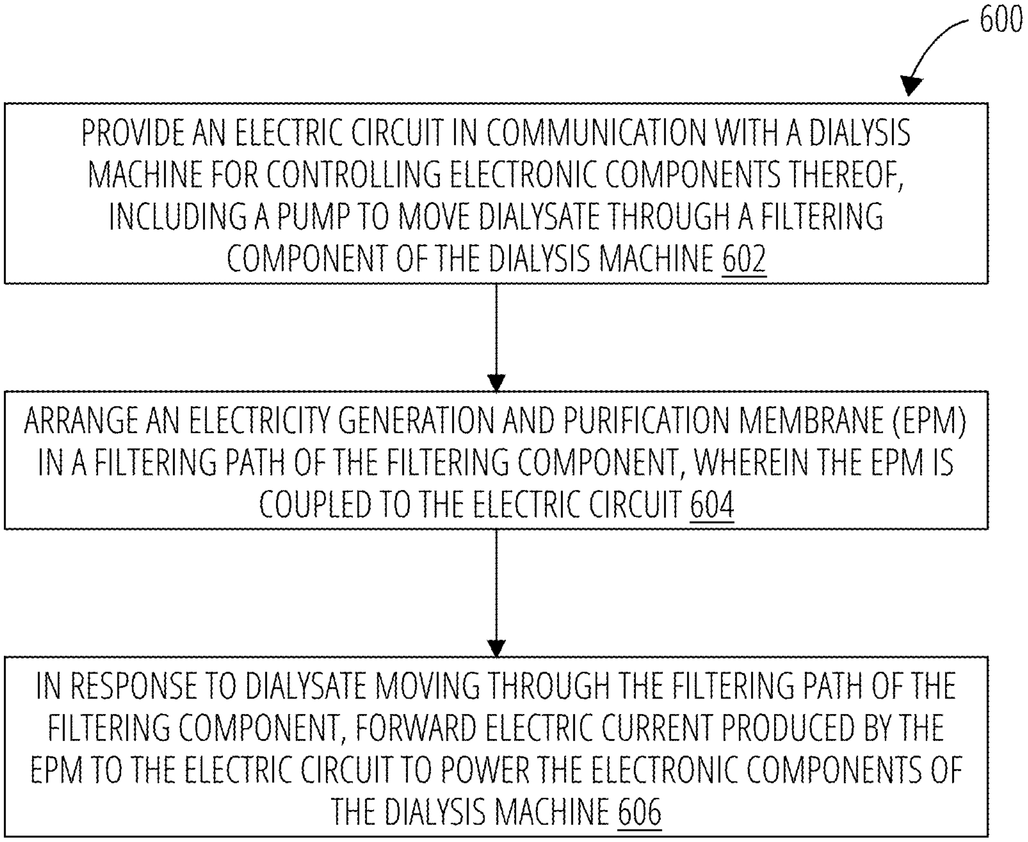
FIG. 6 is a flow chart illustrating an exemplary embodiment of a method in accordance with one or more features of the present disclosure.

FIG. 6 is a flow chart illustrating steps in an example method 600 for dialysis effluent power harvesting. As shown at block 602, in some embodiments, method 600 includes providing an electric circuit in communication with a dialysis machine for controlling electronic components thereof, including a pump of the dialysis machine. As shown at block 604, in some embodiments, method 600 includes arranging an electricity generation and purification membrane (EPM) in a filtering path of a filtering component of the dialysis machine, wherein the EPM is coupled to the electric circuit. As shown at block 606, in some embodiments, method 600 includes, in response to dialysate moving through the filtering path of the filtering component, forwarding electric current produced by the EPM to the electric circuit to power the electronic components of the dialysis machine.

The systems and methods described herein have been explained in connection with dialysis machines having a particular configuration. It is contemplated that the systems described herein may be used with dialysis machines having other configurations, for example, different types of dialysis machines and/or dialysis machines having dialysate heaters in other configurations. The systems described herein may be used with any appropriate dialysis machine.

Some embodiments of the disclosed system may be implemented, for example, using a storage medium, a computer-readable medium or an article of manufacture which may store an instruction or a set of instructions that, when executed by a machine (e.g., processor, processing circuit, or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

While the systems and techniques described herein for pre-heating dialysate for a dialysis machine have been largely explained with reference to a dialysis machine, in particular, a hemodialysis machine, the systems and techniques described for pre-heating dialysate may be used in connection with other types of medical treatment systems and/or machines, such as a peritoneal machine or other medical treatment device involving medical fluids. In some implementations, the dialysis machine may be configured for use in a dialysis clinic or a patient's home (e.g., a home dialysis machine). The home dialysis machine can take the form of a peritoneal dialysis machine or a home hemodialysis machine.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A kidney dialysis system comprising:

a dialysis machine comprising a pump configured to move dialysate through a filtering component of the dialysis machine;

an electric circuit in communication with the dialysis machine and configured to control electronic components, including the pump, of the dialysis machine;

wherein the filtering component includes an electricity generation and purification membrane (EPM) in a filtering path of the filtering component, wherein the EPM is coupled to the electric circuit; and wherein the EPM is configured to generate electricity in response to dialysate moving through the filtering path of the filtering component and provide the generated electricity to the electric circuit to power the electronic components of the dialysis machine.

2. The system of claim 1, wherein the dialysis machine includes a sorbent cartridge configured to refresh dialysate; and wherein the filtering component includes the sorbent cartridge and the EPM is positioned at an ingress port, an egress port, or a combination thereof, of the sorbent cartridge such that dialysate flows through the EPM before exiting the sorbent cartridge.

3. The system of claim 1, wherein the filtering component comprises a dialyzer and the EPM is positioned in a dialysate flow path of the dialyzer.

4. The system of claim 3, wherein the dialyzer comprises:

an outer housing including an ingress blood port, an egress blood port, an ingress dialysate port, and an egress dialysate port; and an internal chamber comprising a plurality of tubes extending between the ingress blood port and the egress blood port, wherein the plurality of tubes are arranged and configured to move the blood from the ingress blood port to the egress blood port, and the plurality of tubes are made of semi-permeable membranes to enable waste to exit the semi-permeable membrane, but allow blood to stay within the tubes;

wherein the dialysate flow path includes the dialysate flowing around the plurality of tubes to carry the waste out the semi-permeable membrane, away from the blood, and out the internal chamber through the egress dialysate port;

wherein the EPM is positioned within the internal chamber such that the dialysate flows through the EPM to get to the egress dialysate port.

5. The system of claim 1, wherein the EPM comprises at least a first layer comprising a conductive polymer and a second layer comprising a porous filter configured to remove waste from the dialysate and desilt dialysate passing therethrough.

6. The system of claim 5, wherein the conductive polymer comprises water-streaming carbon nanotubes configured such that, as dialysate flows through the first layer, the water-streaming carbon nanotubes generate a movement of ions across the first layer of the EPM in a direction that is perpendicular to a flow of dialysate through the EPM, the movement of ions generating the electricity that is provided to the electric circuit.

7. The system of claim 6, wherein the EPM further includes a poly(acrylic acid)/carboxymethyl cellulose (PAA/CMC) binder.

8. The system of claim 1, wherein the electronic components include an ultraviolet (UV) light emitting diode (LED) powered by the electricity provided by the EPM, the UV LED positioned in the filtering path of the dialysate and configured to destroy bacteria and viruses in the dialysate; or wherein the electronic components are configured to produce an electric field around a portion of the filtering path to remove toxins from the dialysate.

9. The system of claim 1, wherein the filtering component comprises a dialyzer and wherein the electronic components include one or more ultrasonic heads positioned within the dialyzer and configured to eliminate air bubbles in the dialysate.

10. A wearable or portable kidney dialysis system comprising:

a dialysis machine comprising a pump configured to move dialysate through a filtering component of the dialysis machine;

an electric circuit in communication with the dialysis machine and configured to control electronic components, including the pump, of the dialysis machine;

wherein the filtering component includes an electricity generation and purification membrane (EPM) in a filtering path of the filtering component, wherein the EPM is coupled to the electric circuit; and wherein the EPM is configured to generate electricity in response to dialysate moving through the filtering path of the filtering component and provide the generated electricity to the electric circuit to power the electronic components of the dialysis machine.

11. The system of claim 10, wherein the wearable or portable kidney dialysis system is integrated into one or more of the following:

a wearable belt;

a backpack;

a waist pack; and a vest configured to be wearable around a person's back and torso.

12. The system of claim 11, wherein the wearable or portable kidney dialysis system further comprises a kinetic-based power generator configured to initially power the pump to start dialysate flowing therethrough, the kinetic-based power generator configured to provide power to the electric circuit as a patient wearing the wearable belt moves.

13. The system of claim 10, wherein the dialysis machine includes a sorbent cartridge configured to refresh dialysate; and wherein the filtering component includes the sorbent cartridge and the EPM is positioned at an ingress port, an egress port, or a combination thereof, of the sorbent cartridge such that dialysate flows through the EPM before exiting the sorbent cartridge.

14. The system of claim 10, wherein the filtering component comprises a dialyzer and the EPM is positioned in a dialysate flow path of the dialyzer.

15. The system of claim 14, wherein the dialyzer comprises:

an outer housing including an ingress blood port, an egress blood port, an ingress dialysate port, and an egress dialysate port; and an internal chamber comprising a plurality of tubes extending between the ingress blood port and the egress blood port, wherein the plurality of tubes are arranged and configured to move the blood from the ingress blood port to the egress blood port, and the plurality of tubes are made of semi-permeable membranes to enable waste to exit the semi-permeable membrane, but allow blood to stay within the tubes;

wherein the dialysate flow path extends around the plurality of tubes such that, during operation of the dialysis system, the dialysate carries the waste out the semi-permeable membrane, away from the blood, and out the internal chamber through the egress dialysate port;

wherein the EPM is positioned within the internal chamber such that, during operation of the dialysis system, the dialysate flows through the EPM to get to the egress dialysate port.

16. The system of claim 10, wherein the EPM comprises at least a first layer comprising a conductive polymer and a second layer, the second layer comprising a porous filter configured to remove waste from the dialysate and desilt dialysate passing therethrough.

17. The system of claim 16, wherein the conductive polymer comprises water-streaming carbon nanotubes configured such that, as dialysate flows through the first layer, the water-streaming carbon nanotubes generate a movement of ions across the first layer of the EPM in a direction that is perpendicular to a flow of dialysate through the EPM, the movement of ions generating the electricity that is provided to the electric circuit;

wherein the EPM further includes a poly(acrylic acid)/carboxymethyl cellulose (PAA/CMC) binder.

18. The system of claim 10, wherein the pump of the dialysis machine includes a low power micropump configured to pump dialysate and blood through the dialysis machine.

19. The system of claim 10, wherein the electronic components include an ultraviolet (UV) light emitting diode (LED) powered by the electricity provided by the EPM, the UV LED positioned in the filtering path of the dialysate and configured to destroy bacteria and viruses in the dialysate; or wherein the electronic components are configured to produce an electric field around a portion of the filtering path to remove toxins from the dialysate; or wherein the filtering component comprises a dialyzer and wherein the electronic components include one or more ultrasonic heads positioned within the dialyzer and configured to eliminate air bubbles in the dialysate.

20. A method of powering electronic components in a dialysis machine for renal filtration comprising a pump to move dialysate through a filtering component of the dialysis machine, the method comprising:

providing an electric circuit in communication with the dialysis machine for controlling electronic components thereof, including the pump;

arranging an electricity generation and purification membrane (EPM) in a filtering path of the filtering component, wherein the EPM is coupled to the electric circuit; and in response to dialysate moving through the filtering path of the filtering component, forwarding electric current produced by the EPM to the electric circuit to power the electronic components of the dialysis machine.

* * * * *